(12) United States Patent
Martino et al.

(10) Patent No.: US 6,888,636 B2
(45) Date of Patent: *May 3, 2005

(54) METHOD AND APPARATUS FOR MEASURING THE COLOR PROPERTIES OF FLUIDS

(75) Inventors: Anthony Joseph Martino, West Chester, PA (US); Ken Stephen Schermacher, Chadds Ford, PA (US); Larry Eugene Steenhoek, Wilmington, DE (US); Timothy Aaron Snyder, Voorhees, NJ (US); Robert Averitt, Newark, DE (US); Robert E. Bucher, Jr., Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 37 days.

This patent is subject to a terminal disclaimer.

(21) Appl. No.: 10/097,676

(22) Filed: Mar. 13, 2002

(65) Prior Publication Data

US 2002/0149773 A1 Oct. 17, 2002

Related U.S. Application Data

(60) Provisional application No. 60/276,967, filed on Mar. 19, 2001.

(51) Int. Cl.[7] ............................................... G01N 21/00
(52) U.S. Cl. ...................... 356/436; 356/319; 356/409
(58) Field of Search ................................ 356/432–438, 356/319, 402, 407–411, 414–417, 421, 425, 236, 73; 250/432–438; 422/67, 81

(56) References Cited

U.S. PATENT DOCUMENTS 3,952,577 A * 4/1976 Hayes et al. ................ 73/54.04
4,038,030 A * 7/1977 Albright et al. ............ 436/165

(Continued)

FOREIGN PATENT DOCUMENTS

| BR | PI9800361-5 | 2/1998 |
|---|---|---|
| DE | 25 25 701 A1 | 12/1976 |
| DE | 240 075 A1 | 10/1986 |
| DE | 197 20 936 A1 | 1/1999 |
| EP | 0 167 750 A2 | 1/1986 |
| FR | 2 594 131 A1 | 8/1987 |
| GB | 884 863 | 12/1961 |
| GB | 1 589 705 | 5/1981 |
| SU | 364877 | 11/1973 |
| WO | WO 97/28477 A1 | 8/1997 |
| WO | WO 99/48602 A1 | 9/1999 |

OTHER PUBLICATIONS

Anonymous Colour measuring of wet coating compositions. Research Disclosure—Nov. 1991, RD 33196.

Copy of International Search Report dated Sep. 24, 2002.

*Primary Examiner*—Gregory J. Toatley, Jr.
*Assistant Examiner*—Sang H. Nguyen
(74) *Attorney, Agent, or Firm*—Steven C. Benjamin

(57) ABSTRACT

An apparatus for inspection of fluids having a fluid analysis cell with a cavity therein enclosed by two light transmitting windows and having a spacer member fixedly positioned therebetween which provides a fluid analysis chamber of fixed pathlength where fluid flows by the windows and preferably wherein the flow laminar and at a uniform shear to provide accurate color measurements. Light transmitting and receiving probes are positioned adjacent to the viewing windows and wherein the faces of each probe are contiguous and flush with the viewing windows but are separated from the flow by the viewing windows, so that transmission measurements can be taken orthogonal to the direction of flow. The apparatus is particularly useful in the manufacture of dispersions and tints used in the manufacture of paints, so that the color of material being made can be accurately matched to a standard color in the wet state with confidence that the color will match in the dry state.

16 Claims, 10 Drawing Sheets

U.S. PATENT DOCUMENTS

| | | | | |
|---|---|---|---|---|
| 4,180,739 A | * | 12/1979 | Abu-Shumays | 250/461.1 |
| 4,278,887 A | * | 7/1981 | Lipshutz et al. | 250/432 R |
| 4,403,866 A | | 9/1983 | Falcoff et al. | |
| 4,511,251 A | | 4/1985 | Falcoff et al. | |
| 4,575,424 A | * | 3/1986 | Allington et al. | 210/198.2 |
| 4,761,074 A | * | 8/1988 | Kohsaka et al. | 356/37 |
| 4,887,217 A | | 12/1989 | Sherman et al. | |
| 4,890,920 A | | 1/1990 | Niziolek et al. | |
| 4,936,685 A | | 6/1990 | Taylor et al. | |
| 5,304,492 A | * | 4/1994 | Klinkhammer | 436/52 |
| 5,442,437 A | * | 8/1995 | Davidson | 356/246 |
| 5,606,412 A | * | 2/1997 | Saito et al. | 356/246 |
| 5,608,517 A | * | 3/1997 | Munk | 356/246 |
| 5,919,712 A | * | 7/1999 | Herron et al. | 436/518 |
| 6,288,783 B1 | | 9/2001 | Auad | |
| 6,400,453 B1 | * | 6/2002 | Hansen | 356/237.1 |
| 6,449,040 B1 | * | 9/2002 | Fujita | 356/319 |

\* cited by examiner

METHOD AND APPARATUS FOR MEASURING THE COLOR PROPERTIES OF FLUIDS

CROSS-REFERENCE TO RELATED APPLICATION

This application claims priority under 35 U.S.C. §119 from U.S. Provisional Application Ser. No. 60/276,967 (filed Mar. 19, 2001), which is incorporated by reference herein for all purposes as if fully set forth.

BACKGROUND OF THE INVENTION

This invention relates to a method of and apparatus for the inspection of fluids. In particular, the invention relates to an improved apparatus for measuring the color properties of fluids in transmission and/or reflection, such as paint dispersions and tints flowing through the apparatus.

Pigment dispersions and tints are widely used nowadays in formulating high performance coating compositions used in particular for exterior finishes for automobiles and trucks.

In the manufacture of such dispersions and tints, one problem is to measure the color and strength of the material as it is being made, so that adjustments can be quickly made to bring this material within acceptable color tolerance values. Color measurements nowadays are carried out by a manual process, which involves taking an aliquot of the material, blending it with a standard white or black paint, spraying out the blends as a coating onto panels, baking and drying the panels, and then measuring one or more color properties of the dried coating using a colorimeter or spectrophotometer against a standard. Adjustments are then made to the batch until the color parameters match those of the standard.

Color measurements by this method are very time consuming because of sample preparation and drying times. Also, this procedure may have to be repeated numerous times before the desired color property is achieved. Another problem which arises with this procedure is that the accuracy of the test is dependent on the color and strength stability of the standard white or black paints. Even with careful control, these standards tend to vary from batch to batch and also tend to flocculate or settle in time, leading to poor test repeatability and making it very difficult to accurately analyze the color and strength of the batch as it is being made.

The aim within the industry for some time has been to measure the color properties of these fluids in a wet state and in a way which predicts the color of the fluid when applied and dried. The primary benefits are mainly associated with time savings although some are associated with the increased likelihood of an automated manufacturing process.

For measuring in transmission, conventional laboratory spectrophotometers, employing cuvette-type sample chambers, have been proposed to make such wet measurements off-line by measuring a transmission spectrum of a wet transparent sample. However, cell pathlengths in such spectrophotometers are, in general, too large for such measurements, as these fluids tend to be too optically dense. Moreover, settling and flocculation can also occur, changing the color of the sample. Additionally, simply taking a sample of wet fluid and putting it in a glass cell and measuring its color properties generally leads to inconsistent results, mostly due to poor repeatability and operator variability.

For measuring in reflection mode, one might propose using a conventional colorimeter to measure the free surface of a wet coating of fluids such as pigment dispersions or tints. However, surface non-uniformities of such coatings, as well as settling, flocculation, and lack of hiding would still lead to erroneous results and unacceptable measurement variability. Moreover, coupling such a device to a wet sample has its own difficulties, including but not limited to, operation of said device in the presence of volatile flammable solvents emitted from the sample surface.

Another instrument, described in Batista et al. WO 98/16822, published Apr. 23, 1998, employing a variable pathlength fluid measurement cell to measure properties of fluids, including color, could be used for such measurements. However, this equipment possesses multiple moving parts which are part of the fluid path, which can cause difficulty in cleaning, and are difficult to maintain. Another disadvantage is that the design is such that it requires high volumes of fluid sample to take proper readings.

Therefore, there is still a need to provide a method and apparatus for color measurement of wet fluids that: produces acceptably consistent results; does not require the spraying and blending with white or black standards and the production of a number of dry samples; cleans rapidly (within 1 or 2 minutes) so that the cycle time of the measurement is extremely small compared to process changes; provides an easy means (including automatic) of delivering sample to the analysis cell so that fluid measurements of color and strength can be made rapidly; and predicts with confidence that the wet readings will also match the standard in the dry.

In addition to the above features, there is also a need to provide a method and apparatus that can be made intrinsically safe, so that it can be placed on a plant floor in an environment wherein may be contained an explosive atmosphere

SUMMARY OF THE INVENTION

An apparatus for inspection of fluids having the following components:

a fluid analysis cell having a cavity therein;

an upper and lower light transmitting window enclosing opposite ends of the cavity;

a spacer having an annular side wall fixedly positioned in said cavity between said upper and lower viewing windows providing a fluid chamber where fluid flows between said windows;

a fluid inlet and outlet channel connected in fluid communication with said fluid chamber to enable fluid to flow into and out of said fluid chamber, preferably the flow of fluid through the chamber being unidirectional laminar flow at uniform shear;

an optional pressure vessel, in which a fluid sample is placed, and which, by means of pressurization, delivers the sample to the fluid analysis cell;

an optional second pressure vessel, in which cleaning solvent is placed, and which, by means of pressurization, delivers the solvent to the fluid analysis cell for cleanout of the cell and fluid sample lines;

a light transmitting and a light receiving probe positioned in any order above and below the upper and lower viewing windows, wherein the faces of each probe are contiguous and flush with the viewing windows and are thus orthogonal to the direction of flow but separated from the flow by the viewing windows, so that direct transmission measurements can be taken orthogonal to the direction of flow; and, a light source and a spectrophotometer, preferably a flash lamp and a dual beam spectrophotometer, associated with and connected to the probes for directing light to the fluid analysis cell and detecting light therefrom respectively to measure color parameters of the fluid passing through the viewing windows by transmittance and/or reflectance.

In another embodiment, the transmission probe may be replaced by a fiber optic bundle.

In a further embodiment, the transmission probe or fiber optic bundle is interfaced to an integrating sphere having one of its portals contiguous with one of the fluid analysis cell viewing windows so that diffuse or direct transmittance measurements can be made on the fluid sample being analyzed.

In yet another embodiment, an additional probe is positioned at an angle normal to the fluid sample so that reflectance measurements can also be made on the fluid sample being analyzed.

In still a further embodiment, one of the viewing windows in the fluid analysis cell is replaced with a cylinder of like material transparent to visible light which has one or more facets at angles other than parallel to the surface of the fluid sample, with said facets cut into the surface distal from and parallel to the surface of the fluid sample for interfacing with one or more additional optical probes for measurement in reflectance of the fluid sample being analyzed.

The inspection apparatus also preferably includes the following components:

a purged explosion-proof enclosure for containing all electrical/ electronic components, as well as the light source for the instrument; and an automatic pneumatically-controlled sample system for delivery of the sample to the fluid analysis chamber.

A method for measuring the color properties of a fluid using the above apparatus is also a part of this invention.

DETAILED DESCRIPTION OF THE PREFERRED EMBODIMENTS

In general, the apparatus of the invention can be used to inspect a wide variety of fluids but is designed particularly to measure the color properties of dispersions and tints that are used in the manufacture of high performance automotive coatings. The apparatus is specifically designed to measure the color properties of the fluids flowing through the apparatus using wet light transmittance and/or reflectance measurements over the visible spectrum in a way that produces accurate instrumental readings.

Figure 1:
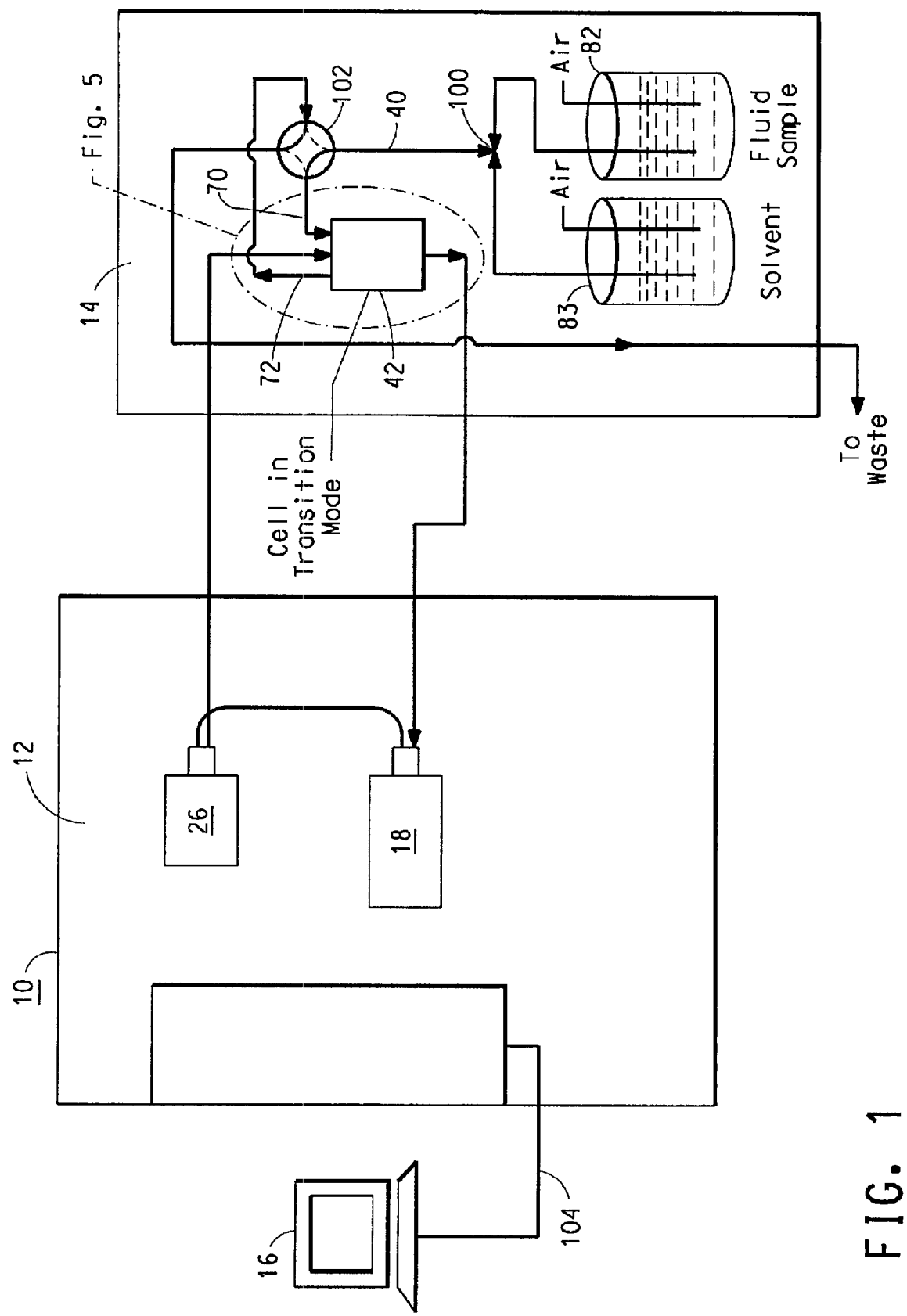
FIG. 1 is a schematic view of the apparatus in accordance with the invention.
Figure 2:
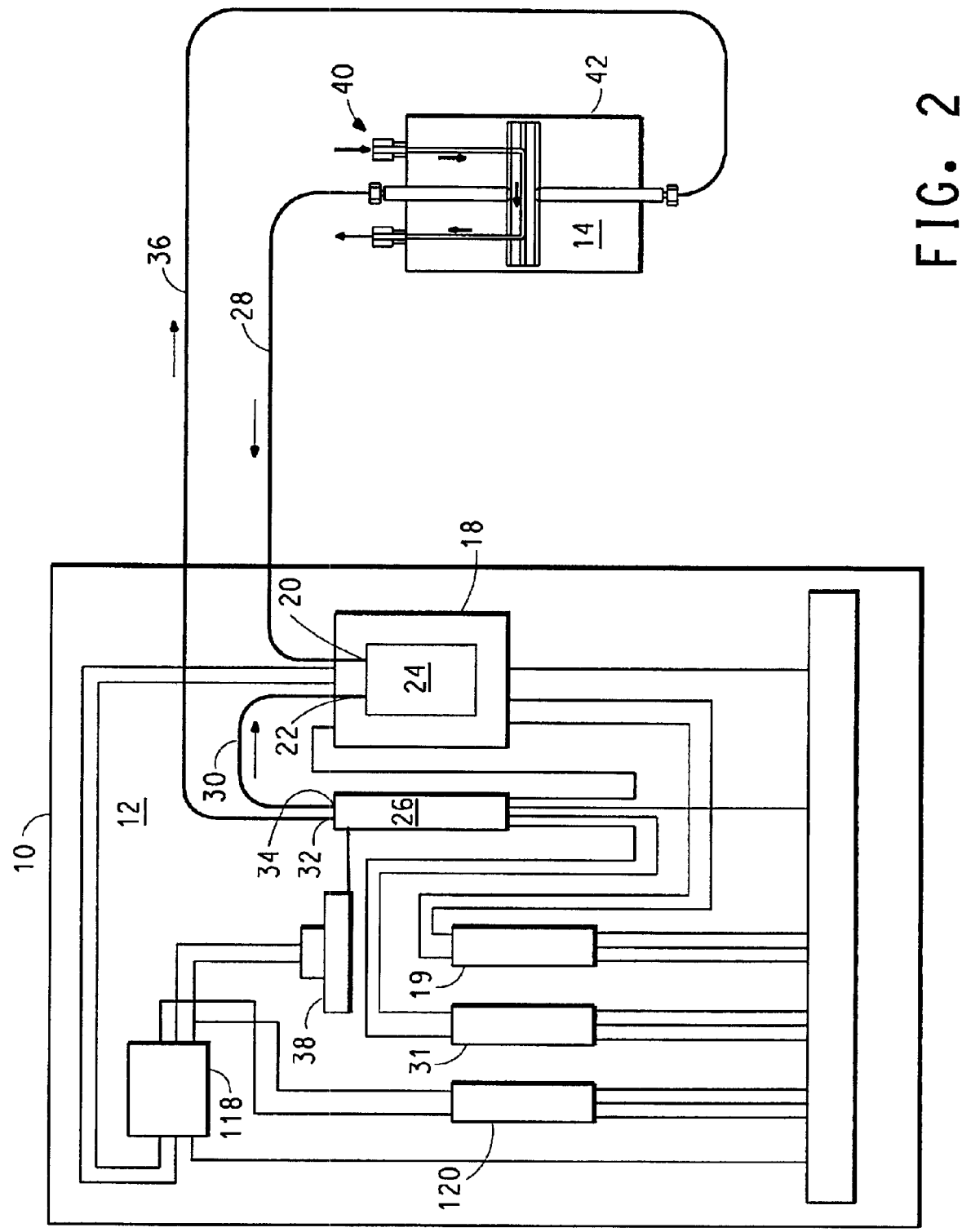
FIG. 2 is a partial front view of the the apparatus of FIG. 1 showing only the optical unit and fluid analysis cell.

Referring now to FIGS. 1 and 2 of the drawings, the apparatus according to the invention comprises a housing 10 which contains an optical unit 12, for providing a source of visible light to a fluid analysis unit 14 and for detecting the visible light emitted therefrom. Both the optical unit 12 and fluid analysis unit 14 are connected to a system control unit, preferably a computer, 16 for data acquisition, spectral analysis, and control of the functions of units 12 and 14.

The optical unit 12 preferably comprises a dual beam spectrophotometer 18, preferably powered by a standard power supply 19, and containing two inputs 20 and 22 for receiving light over the visible spectrum from 400 to 700 nanometers (nm), preferably in 10 nm increments, a diffraction grating (not shown) for dispersion of the light signals, and a photodiode array detector 24 (incorporated therein). One input 20 collects light from the fluid sample under analysis, while the other 22 collects light directly from light source 26, and provides a reference signal, so that corrections may be effected for variations in the light source intensity. Light is provided to inputs 20 and 22, via single-fiber fiber optic cables 28 and 30 through a shroud and shutter assembly (described later) from light source 26. The light source 26 itself preferably comprises a halogen flash lamp, e.g., a xenon flash lamp, that emits collimated light over a range of wavelengths from 400 to 700 nanometers (nm). The lamp is preferably powered by a standard power supply 31.

As shown in FIG. 2, the light source 26 preferably contains two outputs 32 and 34 for emitting visible light. The first output 32 is connected via a single-fiber fiber optic cable 36 to the fluid analysis unit 14, as will be described below, to allow for transmission of light to the fluid sample being tested. The transmitted light beam, after passing through the fluid analysis unit 14, is then directed via single-fiber fiber optic cable 28 to input 20 of the dual beam spectrophotometer 18 for spectral analysis. The second output 34 from the light source serves as a reference channel, which may be used: 1) to calibrate the measurement for lamp intensity fluctuations and correct for them; and 2) to monitor the performance of the flash lamp 26, so that it can be changed as soon as it goes below specification. Accordingly, output 34 is connected via single-fiber fiber optic cable 30 to input 22 of the spectrophotometer to receive light direct from the flash lamp.

The shroud and shutter assembly 38 mentioned above is used to block the light emitted from the output 32 so that a dark current measurement may be made during the photometric calibration step. A set of optical filters (not shown) contained within the flash lamp shroud 102 (shown in FIG. 8) are used to vary the intensity of light emitted from the flash lamp, which: 1) enables the spectrophotometer's detector to make color measurements in its optimum condition, without saturation by high intensity light, or lack of resolution with low intensity light; and 2) ensures that optical signals to both sides of the dual beam spectrophotometer are balanced photometrically. The transmitted light beam, after passing through the fluid analysis unit 14, is ultimately directed to detector 24 (not shown in detail) contained in the dual beam spectrophotometer 18. When the light from either input, 20 or 22, enters the spectrophotometer through its entrance slits, it first strikes a concave reflecting diffraction grating, which disperses the light into its characteristic wavelengths and reflects it to a photodiode array detector. The light from one input then proceeds to one half of the detector array, while the light from the other input proceeds to the other half of the array. The diffraction grating within the spectrophotometer together with the entrance slits thus enables the detector to detect single frequency radiation and defines the wavelength resolution of the spectrophotometer.

The detector 24 is preferably a standard photodiode array detector which comprises a high sensitivity photodiode array connected to a low noise amplifier. The transmitted light is sent to the detector for spectral measurement and the detector signal is then fed preferably via an RS-232 cable (not shown) to the computer 16 for spectral analysis and L*, a*, and b* color value computation, which constitutes the color measurement.

The color technology used for spectral analysis, calculation of the L*, a*, and b* color values of the fluid being tested therefrom, and making color comparisons to a standard is well known and fully described in Falcoff et al. U.S. Pat. No. 4,403,866 issued Sep. 13, 1983, which is hereby incorporated by reference herein.

Referring again to FIG. 1, fluid analysis unit 14 comprises a fluid control unit 40, as will be later described, which supplies a continuous flow of fluid under investigation or reference fluid to a flowthrough fluid analysis cell 42.

Figure 3:
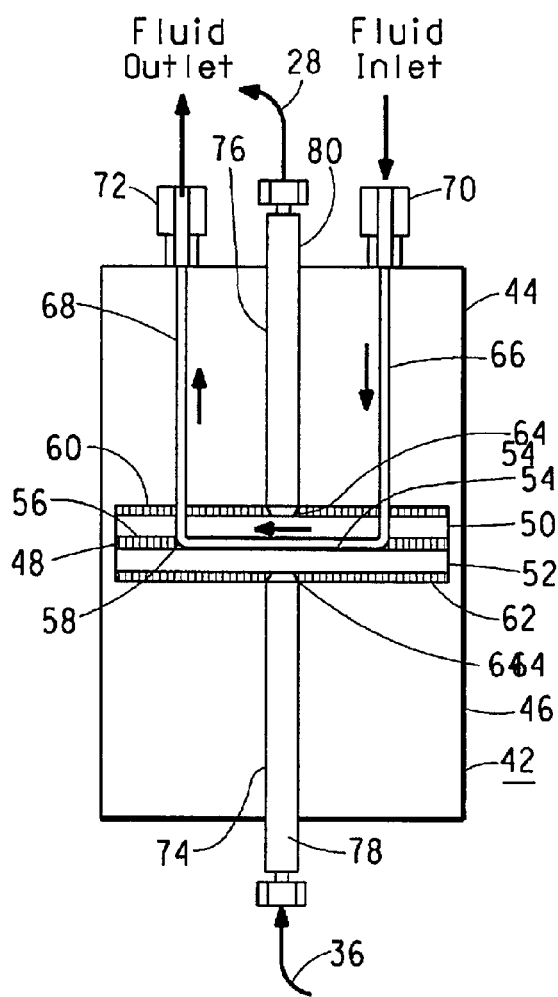
FIG. 3 is a front view of the fluid analysis cell used in the apparatus of FIG. 1.
Figure 4:
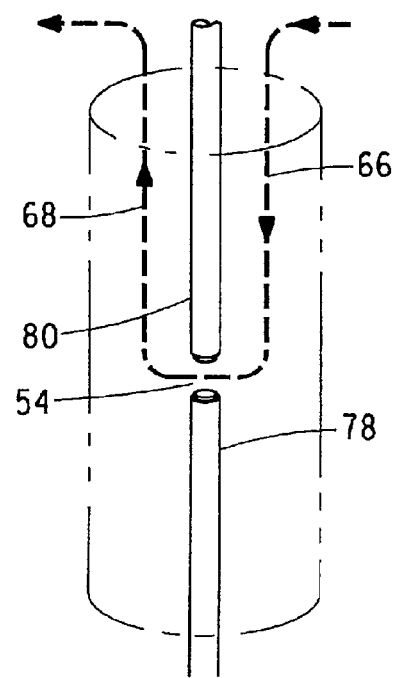
FIG. 4 is a partial view of the fluid analysis cell of FIG. 3 showing fluid flow through the cell.

Referring now to FIGS. 3 and 4, the fluid analysis cell 42 is designed to provide a fluid stream of uniform color so that accurate color measurements can be made. The cell 42 comprises a cylindrical vessel comprised of two halves 44 and 46 that are joined together along the midpoint of the vessel. The lower half 46 of the cell contains a central cavity 48 along its upper surface. Positioned within the cavity in spaced apart relation are upper and lower circular viewing windows 50 and 52, that enclose opposite ends of the cavity and allow for light transmission through the cell.

Positioned between the spaced apart viewing windows is a cavity which forms the fluid analysis chamber 54. As shown in FIG. 3, the fluid analysis chamber 54 is formed by placing an insert or spacer member 56, such as a brass shim, between the viewing windows 50 and 52. The spacer 56 has an annular side wall preferably having an elliptical shape which creates a fluid flow channel therein. The thickness of the spacer 56 determines the cell pathlength, and may be of any size, although for practical reasons (because of absorbance of the samples being measured) a thickness between 1 and 10 mils (0.001 to 0.010 inch) is usually chosen.

Upper and lower circular elastomeric gaskets 60 and 62 are also positioned above and below the viewing windows 50 and 52, respectively, to provide fluid tight seals around the fluid analysis chamber 54. Each gasket 60 and 62 preferably has a circular optical view port 64 at its center to allow light to pass through the viewing windows.

With the above elements placed in the central cavity of the lower half of the cell, the two cylindrical halves 44 and 46 of the cell are secured together and held in place preferably by bolts (not shown) tightened with sufficient force to provide a sealed compartment for the cell, which may withstand hydrostatic/hydrodynamic pressures preferably up to 250 psig.

The cell also includes fluid inlet and outlet channels 66 and 68, respectively, to enable fluid flow into and out of the fluid analysis chamber. As shown in FIG. 3, the inlet and outlet channels 66 and 68 are formed along the upper half of the cell and extend longitudinally downward into the cell and through respective holes in both the upper seal 60 and the upper viewing window 50 to provide fluid flow communication with the fluid analysis chamber 54. The two flow channels are preferably aligned with the two foci of the elliptical hole in the spacer member 56 to provide for unidirectional flow within the analysis chamber. Threaded flow fittings 70 and 72 are preferably screwed into the flow channels along the upper surface of the cell to receive inlet and outlet pipes (not shown).

To complete the cell assembly, the lower and upper halves 46 and 44 of the cell include central channels 74 and 76 which extend along the entire longitudinal axis of each half cell and terminate at the lower and upper viewing windows, respectively. Inserted within the central channels are transmitting and receiving fiber optic probe 78 and 80, respectively, which are connected to fiber optic cables 36 and 28, respectively, which provide a path for light to enter and exit the fluid analysis cell. The probes preferably terminate in optically flat windows made of a durable optical material such as sapphire or quartz, and contain light collimation lenses. The windows are preferably affixed to the ends of the probes with a seal (not shown). The probes 78 and 80 with viewing windows facing each other are inserted in their respective channels and are positioned to extend through the central optical view port 64 in each gasket, so that the face of each probe is contiguous and flush with the cell windows. As the probes themselves terminate in viewing windows that are transparent to visible light, that means that the probe windows or faces are contiguous and flush with the cell windows. Thus, the probes are placed orthogonal to the direction of flow, but separated from the flow by means of the viewing windows. The axial alignment of the probes enables direct transmission measurements. To maintain proper alignment, the probes are preferably held in place with a set screw (not shown) further back along their axes. Coupling may further be enhanced by an index matching gel between the probe window and the cell window.

The components, as described above, that are used to form the transmission cell 42 should be made of materials which are non-reactive with the fluid that is being passed through the apparatus. Typically the structural components such as the cell halves, spacer, fittings, and probes are made of brass, aluminum, hastelloy, or stainless steel and the viewing windows and probe windows are made of borosilicate glass, quartz, or sapphire. The viewing windows may also be coated with a fluorocarbon polymer to prevent fluid build-up on the cell.

In operation, as shown in FIG. 4, as the fluid passes across and between the viewing windows, it spreads out into roughly a laminar flow pattern, so that optical transmission measurements may be made perpendicular to the direction of flow.

The transmission cell 42 of the present invention, as described above, can thus be characterized as a zero bypass cell, which means that all fluid entering is exposed to the viewing windows. Zero bypass enables sample to flow through the cell at a uniform shear to provide a constant interface that can be measured and at a sufficient velocity to prevent a build-up on the cell window. The chamber is further designed to provide flow through the chamber in a laminar fashion, which prevents settling or flocculation of any pigment suspended in the fluid and which provides a sample of uniform color in the viewing area to insure uniform color measurements. The zero bypass cell also guarantees that all of the fluid will cross the optical view path so as to give a true sample of the fluid.

Another feature of the cell used in the present invention is that the pathlength of light through the sample is fixed but can be set manually by a change in the shim spacer 56 in the cell. Pathlength of the light through the sample is set small enough to allow sufficient light throughput to be accurately measured by the instrument detectors, yet large enough to avoid saturation of the detectors. This enables measurement of transparent as well as opaque fluids. As indicated above, the pathlength is typically set between 1 and 10 mils. However, for some optically dense dispersions or tints, dilution may be necessary to obtain full spectral information. Diffuse transmittance or reflectance measurements as described below may also need to be taken to obtain meaningful spectral data for some samples which have high amounts of light scatterers.

Temperature of the measurement cell and the liquid within the cell is preferably held to a narrow enough range (e.g., plus or minus 5° C.) such that thermal expansion does not change the effective pathlength and such that the standard and sample readings are comparable. Temperature control in the present invention is preferably provided by a thermoelectric or vortex-type cooler (not shown) disposed next to the cell to insure a constant temperature of fluid passing through the cell. The test sample and liquid standard should also be measured at the same temperature within this range to insure uniformity.

Referring again to FIG. 1, the apparatus of this invention also includes a fluid flow control unit 40. Generally any type of control unit can be provided which pumps fluid at a uniform velocity into the apparatus through the inlet 70 and into the fluid chamber 54 formed by the spacer 56 and across the viewing windows of probes 78 and 80 and out through the outlet 72. Color measurements can then be made through the windows by transmittance as a sample volume of fluid is passing through the cell.

In the preferred embodiment, as mentioned above, light is generated by a flashlamp 26, triggered by the spectrophotometer/detector 18, and is introduced to the sample region by means of single-fiber fiber optic cable 36, terminated in probes 78 and 80 held tight against the cell windows by means of set screws in the cylindrical body of the cell 42.

Figure 5:
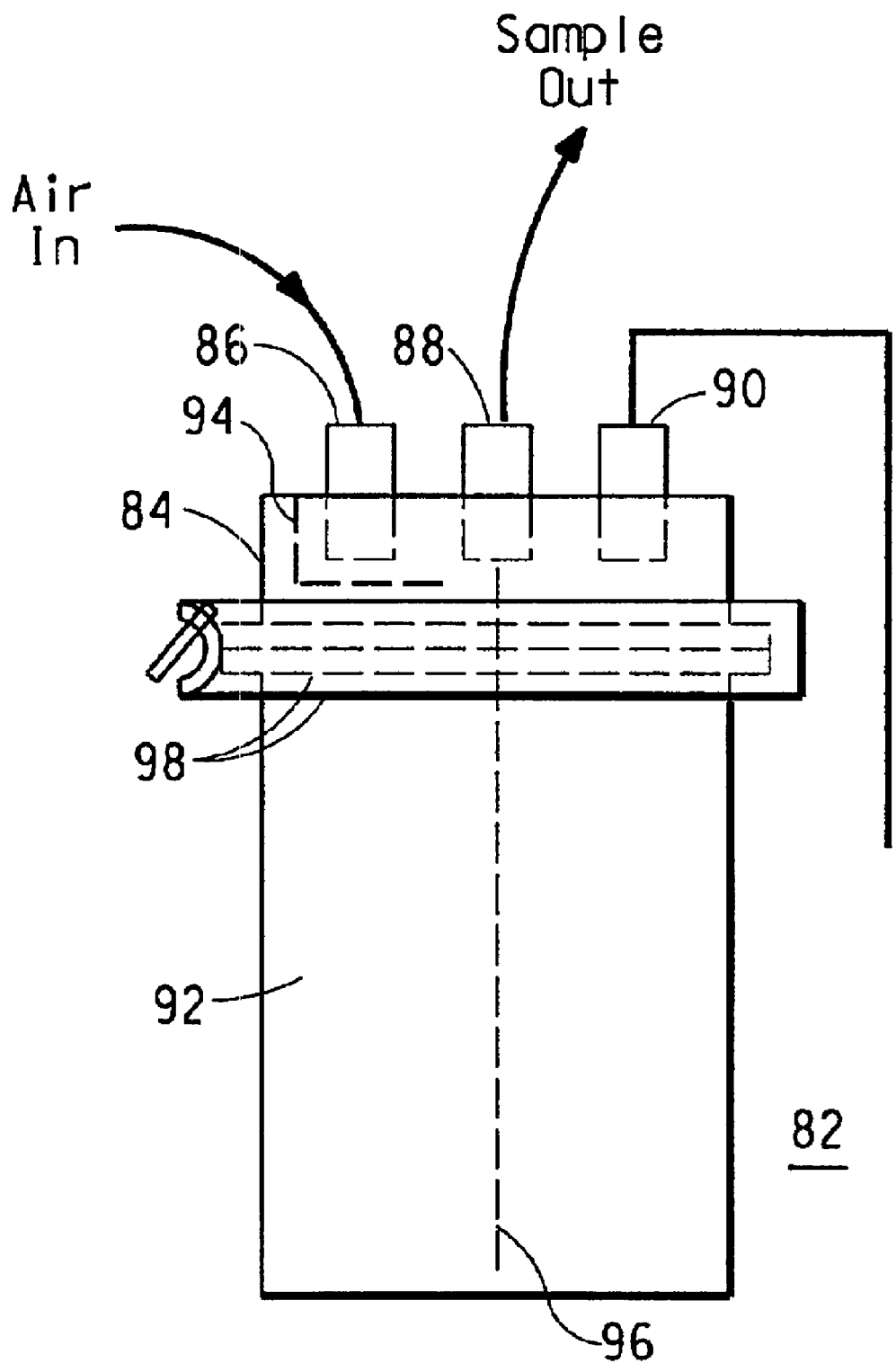
FIG. 5 is a front view of the pressure pot assembly used in the apparatus of FIG. 1.

Fluids such as liquid tints or dispersions are forced into the cell preferably under pressure (approximately 60–80 psig), which is preferably accomplished by means of a sample pressure pot 82. As shown in FIG. 5, the pressure pot 82 itself consists of a lid 84, which serves as the cover and contains the air inlet 86, fluid sample outlet 88, and pressure relief valve 90, and a sample pot 92 which contains the sample. The air inlet 86 is shielded from the sample by a baffle 94 to avoid the formation of bubbles or froth in the sample. The sample outlet 88 is connected on the underside to a dip tube 96, which extends to the bottom of the pot when the two pieces 84 and 92 of the pressure pot are assembled.

The two halves of the pressure pot are preferably sealed with a Teflon-coated neoprene gasket (not shown), which is contained between the two halves. After placing the sample pot 92 with gasket underneath the lid 84, the two halves are brought together and sealed by means of a bracket 98, which when tightened, brings both halves of the pressure pot assembly together. Thus, as air enters the pressure pot assembly 82 from the top, sample is forced up the dip tube 96 and out of the pressure pot, into the sample system of the apparatus, and consequently to and through the cell 42.

In the embodiment shown in FIG. 1, the fluid control unit 40 comprises a sample system with pneumatic or manual valves 100 and 102 and one or more pressure pots 82 and 83 which provide for introduction of sample into the cell and for sample line cleanout. The fluid control unit itself may preferably be controlled by the same computer 16 which controls the optical unit which gathers the spectral measurements. This can be accomplished via an RS-232 serial link (not shown) through an I/O (Input/Output) rack (not shown), which in turn triggers solenoid valves (not shown), releasing air to the pneumatic components of the sample system. Additional I/O rack modules may preferably be interfaced to pumps, temperature and pressure sensors, and a cabinet purge air supply.

Preferably, the system possesses an explosion-proof NEMA 4 enclosure 10 for all electrical and electronic components as well as the light source. Said enclosure is also purged with air by means of an air purge system (not shown) to a pressure super-ambient with respect to the exterior environment to prevent buildup of an explosive atmosphere, possibly present exterior to the enclosure, within the enclosure.

As shown in FIG. 1, the fluid sample being tested proceeds from the pressure pot 82 directly to the cell through a 3-way valve 100 which can either select sample or clean solvent, and then through a 4-way valve 102 which allows reversal of flow through the cell for cleaning. Cleaning of the cell may be accomplished by means of a second pressure pot assembly 83, constructed exactly as the one aforementioned, and which contains clean solvent. Recirculated solvent, containing a mixture of spent solvent, test fluid, and a surfactant may be used for difficult cleaning situations, and may be introduced through the same pressure pot as the sample. Alternatively, pumps (not shown) connected to solvent and recirculated solvent reservoirs (not shown) may be used in place of the pressure pots for delivery of solvent and recirculated solvent respectively to the fluid analysis cell for cleaning purposes.

Figure 6:
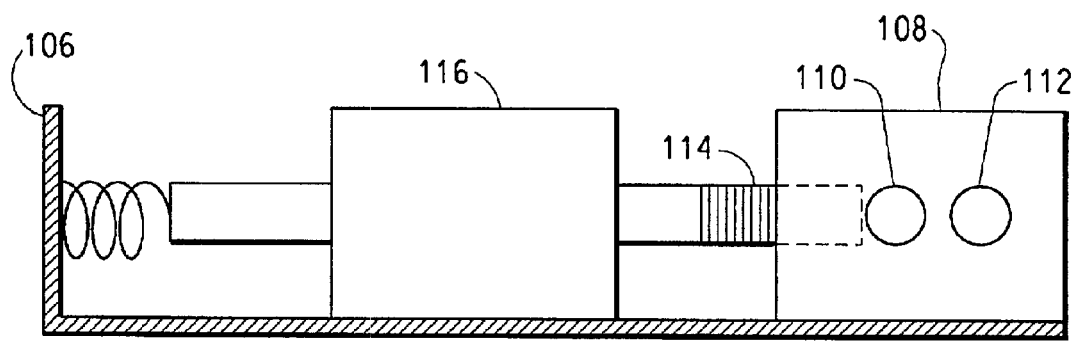
FIG. 6 is a front view of the flash lamp's shroud and shutter assembly containing the outputs for the flash lamp used in the apparatus of FIG. 1.
Figure 7:
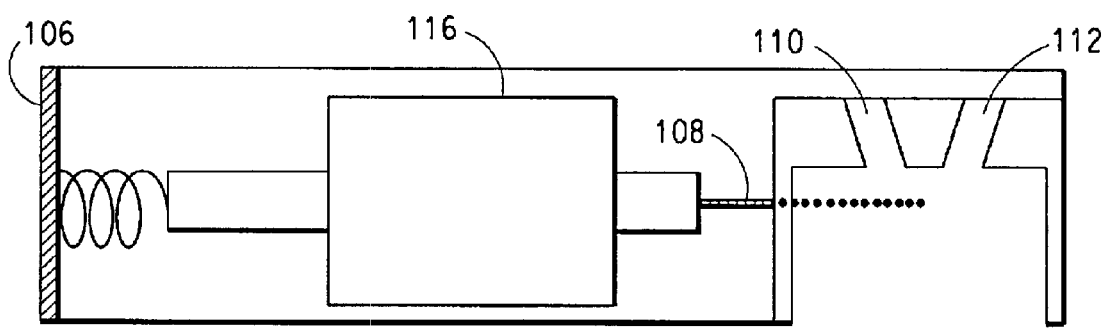
FIG. 7 is a side view of the unit shown in FIG. 6.

Referring again to FIG. 2, the flashlamp 26 in the electronics enclosure 10 preferably consists of a driver pack plus the actual lamp, which is cylindrically shaped. Since the spectrophotometer 18 has two channels 20 and 22, one for sample and one for reference, two fibers 28 and 30 must be coupled to the flash lamp 26 in some way to provide two essentially identical light channels, one of which is coupled to the sample cell 42, while the other is coupled to the reference channel 22 of the spectrophotometer. As shown in FIGS. 6 and 7, a flash lamp shroud/shutter assembly 38 is provided which comprises a bracket 106 which holds a rectangular block shroud 108 with a cylindrical inset hollow and two angular holes 110 and 112 piercing the top of the block into the hollow, and which acts as a cap on the flash lamp 26. The two holes are juxtaposed equidistant from the center of the block. Additionally, the holes 110 and 112 are angled toward the central vertical axis of the block with the target apex of the angle being the lamp filament. In this way, the fiber cables 30 and 36 can be connected to the shroud 108 with both of them aimed at the lamp filament.

To correct for thermal drift of the diode array in the spectrophotometer 18, a "dark" reading is taken during photometric calibration of the spectrophotometer as well as before each sample measurement. The photometric calibration step is normally accomplished for transmission measurements by injecting clean solvent into the cell and measuring the 100 percent transmission line. During a typical sample measurement, the light intensity on the sample channel of the array is corrected for lamp intensity fluctuations by forming a ratio with the intensity at the comparable position on the reference channel. Then, to calculate the transmission, the result is divided by the similar result of the 100 percent line ratio taken during the calibration step. Now, the reference and sample channels 22 and 20, respectively, in a diode array spectrophotometer 18 are really the left and right sides of the same physical array. Because of this fact, in most dual beam spectrophotometers, stray light leakage from the reference channel to the sample channel tends to be problematic when dark samples are being measured in transmission mode, which is often the case when measuring tints and dispersions.

In order to correct for the stray light leakage, a further feature of the apparatus includes a spring loaded shutter assembly, fixedly mounted to bracket 106, and which is attached to the flash lamp shroud 108, so that a spring-loaded shutter 114 may be interjected in front of the sample light port 110 on the flash lamp shroud. Thus, a "dark" reading may be taken on the sample side of the array only, even while the reference side of the array is exposed to full light intensity. This then is actually a measurement of the stray light leakage from the reference 22 to the sample 20 channels. The measurement of the light intensities of both sides of the array, with the sample channel blocked, is taken before every sample measurement to form a "flashing dark" measurement. Since each measurement records the light intensities of both sample and reference channels, the reference channel intensity of the "flashing dark" reading may be ratioed to the intensity of the reference channel in the actual sample measurement to form a scale factor. The scale factor is then applied to the "flashing dark" sample side measurement, and the resultant intensity is then subtracted from the sample side of the actual sample measurement. In this way, the stray light leakage, corrected for lamp intensity fluctuations, is subtracted from the actual sample measurement.

The spring-loaded shutter 114 is translated preferably by an AC/DC solenoid 116, actuated by a AC/DC I/O module 118 (shown in FIG. 2), powered by a standard power supply 120, and triggered by a signal from the spectrophotometer 18.

The transmission data received from the cell is then transferred automatically to the control unit, preferably the computer, 16, wherein the L*, a*, and b* colorimetric calculations are then done. The spectral data and color metrics are then stored for further use and the resultant L*, a*, and b* metrics are reported back to the operator on the computer screen. The interior of the electronics/optics enclosure, along with fiber optic coupling to the sample cell, is shown in FIG. 2.

The apparatus can be used in a variety of chemical processes in which color of the resulting product is measured. It is preferably used in a paint, dispersion, inkjet ink, printing ink, or tint manufacturing process. The apparatus of this invention can be positioned at a remote location from the manufacturing process for either at-line or off-line testing, or can be connected to the production unit for on-line color testing of the wet fluid as it is being made. Allowing the fluid to flow through the cell directly from the processing unit allows for on-line or continuous testing and enables fully automated batch or continuous manufacture of the fluid. The total cycle time of the apparatus as shown in FIG. 1 is a few minutes as opposed to hours using conventional processes. Moreover, it has been found that in making color measurements using this apparatus, there is a good correlation between the color properties of the wet fluid and the corresponding dry coating, which enables visually accurate color matches to be achieved.

A variation of this invention is to use a colorimeter in place of the spectrophotometer.

Figure 8:
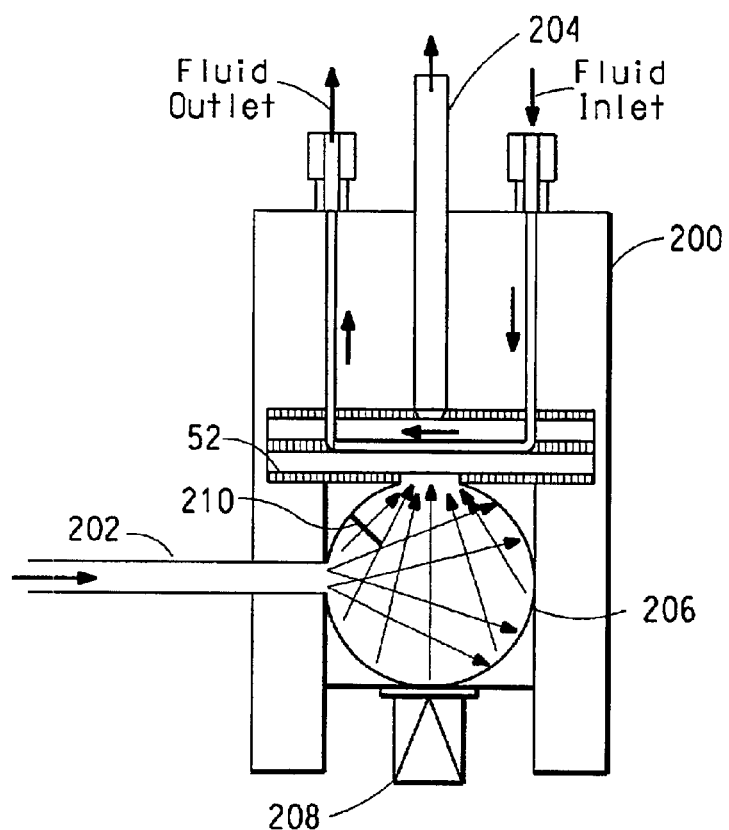
FIG. 8 is a front view of a further fluid analysis cell in accordance with this invention.

In an alternative embodiment of the apparatus of the invention, as shown in FIG. 8, an alternative fluid analysis cell 200 is provided which is essentially the same as that in FIG. 3 described above, but the single-fiber fiber optics are replaced with fiber optic bundles 202 and 204 of the same length and with ¼" ferrule-type connectors. Fiber optic bundle 202 from the light source 26 preferably directs light onto the sample within the fluid analysis chamber 54. This necessitates a slight change in design of the flash lamp shroud 108, and a replacement of the connector on the dual beam spectrophotometer 18 to accommodate these type of connectors. However, the most notable distinguishing feature of this embodiment 200 is the introduction of an integrating sphere 206 within the sample cell for illumination of the sample, both in a specular as well as diffuse manner. This is especially important when the sample contains light scattering pigments and is partially transmitting and partially scattering. Any conventional integrating sphere can be used.

The integrating sphere 206 used herein is preferably 1" in diameter, and coated on the inside with a highly reflective white material, such as barium sulfate or titanium dioxide. The sphere has four portals, three of which preferably are ¼" openings, with the remaining one preferably ½" in diameter. The ½" hole is placed against the lower window 52 inside the cell. The sphere also contains an interior baffle 210 immediately adjacent to the ½" hole and one of the ¼" holes. The illumination fiber bundle 202 is coupled to this ¼" hole to illuminate the sphere, and thereby the sample. The baffle blocks direct, or short-circuit, illumination of the sample by the fiber bundle. The ¼" hole immediately across from the illumination portal is capped with a port plug (not shown) coated with the same white reflective material, thus reflecting direct illumination around the interior of the sphere. The ¼" hole immediately across from the sample opening can be capped with a white-coated port plug (not shown) as well for detection of total light (diffuse+specular), or it can be capped with a "black trap" 208 (a cylindrical cup with an interior cone with its apex at the opening, all coated with a very black absorbing material, such as carbon black) for measurement of diffuse light through the sample. A diagram of the sample cell of this embodiment is shown in FIG. 8.

Figure 9:
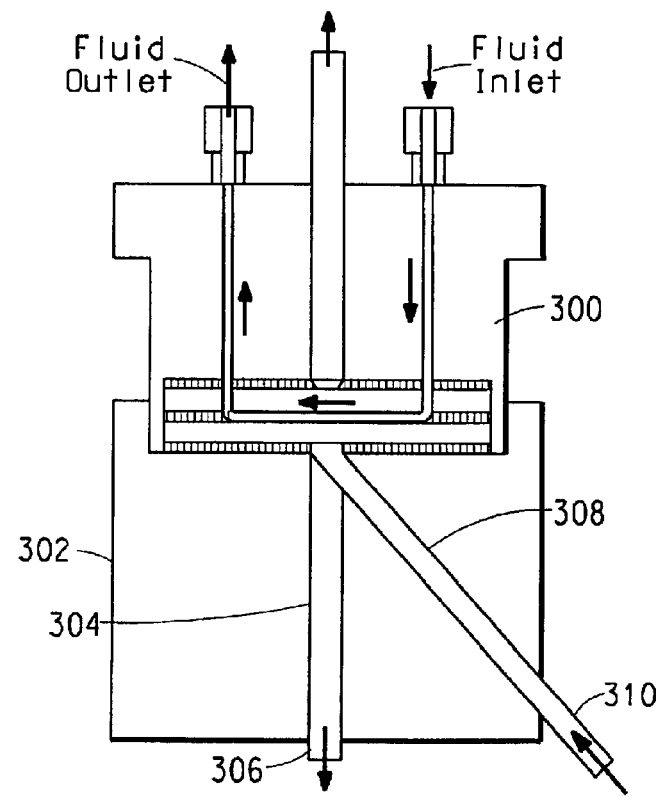
FIG. 9 is a front view of a further fluid analysis cell in accordance with this invention.

In another alternative embodiment of the apparatus of the invention, as shown in FIG. 9, this embodiment is identical to the embodiment 200 described above, with the exception of the sample cell. In this embodiment, the sample cell 300 has for its non-fluid-containing half 302, a probe channel 304 down its axis for the fiber bundle 306, but also has one or more additional probe channels 308 with additional probe(s) 310 at an angle to the axis, where the apex of the angle is on the axis of the cylinder and within the sample itself between the two windows in the cell. In this way, the cell could function as a transmission cell with illumination either at 0 degrees or at an angle from normal to the sample.

The angle is arbitrary, but is preferably 45 degrees for standard 45-0 illumination/detection. As an option, however, the cell could easily be converted to measure in reflection mode by illuminating at an angle to the sample, and detecting normal to the sample on the same side of the sample.

Figure 10:
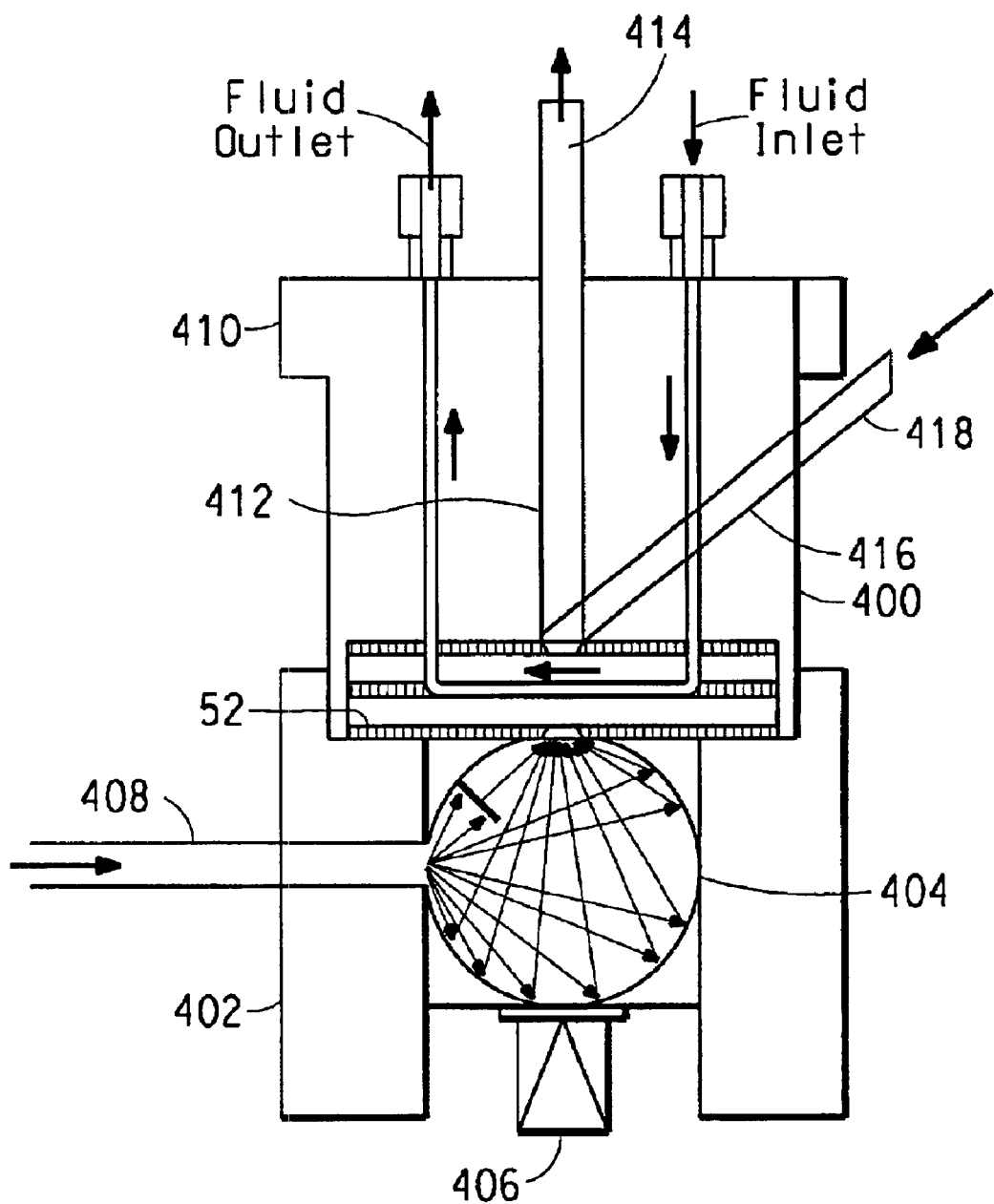
FIG. 10 is a front view of a further fluid analysis cell in accordance with this invention.

In yet another embodiment, as shown in FIG. 10, the apparatus of the invention is the same as embodiment 200, as described above, wherein the cell 400 design incorporates an integrating sphere 402 in the non-fluid-containing half 402, so that transmission measurements may be accomplished using the integrating sphere. As in embodiment 200, the ½" port of the sphere 404 is placed against the lower window 52 of the cell, and possesses a ¼" port opposite the ½" port for incorporation of a white reflector (not shown) or a black trap 406. Fiber bundle 408 from the light source is used for illumination of the sphere as above. However, it also has for its fluid-containing half 410, a probe channel 412 down its axis for the fiber bundle 414, but also has one or more additional probe channels 416 with additional probe(s) 418 at an angle to the axis, where the apex of the angle is on the axis of the cylinder and within the sample itself between the two windows in the cell. Thus reflection measurements would be accomplished using the additional probe 418 at an angle to the cylindrical axis, and detecting normal to the sample with probe 414. As before, the angle can be arbitrary. As above, the rest of the instrumentation remains the same.

Figure 11:
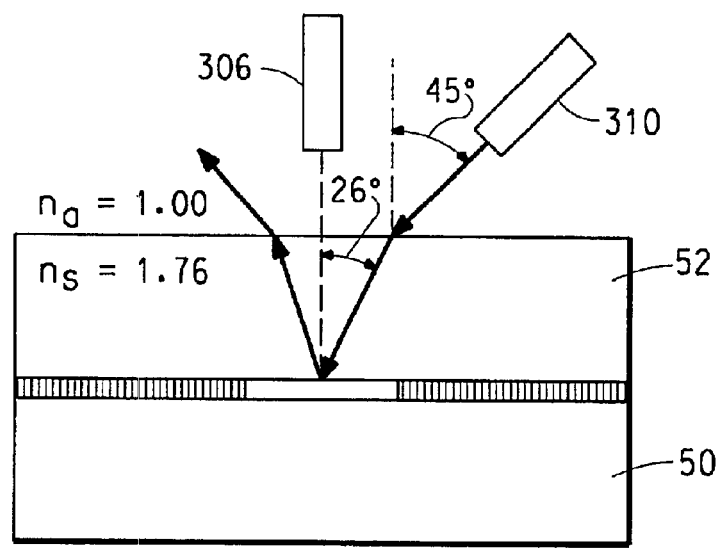
FIG. 11 is a schematic view of the fluid analysis cell windows, showing adjustments that may need to be made to the cell to correct for index of refraction mismatches.

In still yet another embodiment of the apparatus of the invention, an alternative fluid analysis cell is provided identical to that of embodiment 300 above but using reflection mode. Due to the fact that an air interface lies between the fiber optic illuminating bundle 310 and the optical window 52 (of sapphire, quartz, BK7, borosilicate, fused silica or the like), the angle (with respect to normal to the window) of illumination of the sample behind the window is not necessarily the same as the angle of the probe with respect to the cylinder axis. This is due to the index of refraction of the window material. So, for example, in the case of sapphire window material, which has an index of refraction of 1.76, the actual angle (inside the window material) of the illumination impingement on the wet sample must be calculated with Snell's Law, or, $n_a \sin \theta_a = n_s \sin \theta_s$, and would be far different from the assumed angle (in air) on the first surface of the window. A diagram of this situation can be seen in FIG. 11.

Figure 12:
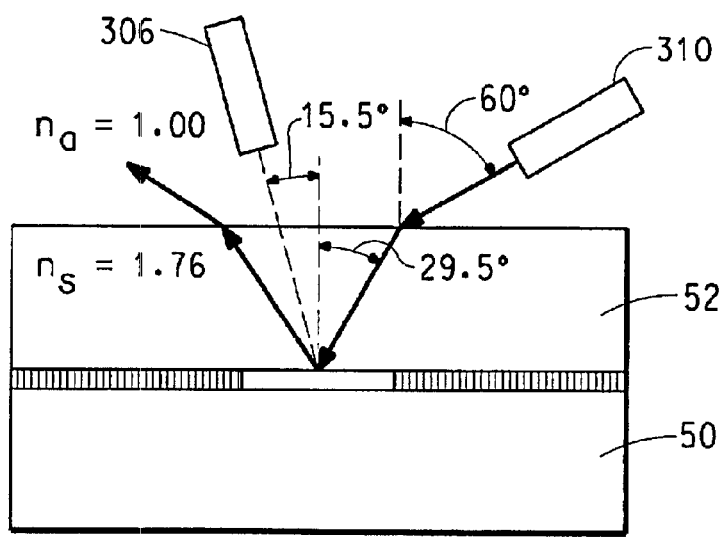
FIG. 12 is another schematic front view of the fluid analysis cell windows, showing adjustments that may need to be made to the cell to correct for index of refraction mismatches.

One means to correct for this index of refraction effect and maintain optical probes which have an oblique aspect with respect to the surface of the window (i.e. with an air/window interface) is to affect the geometry of illumination and detection so that a true 45 degree illumination/detection angle is achieved within the window material. Again using Snell's Law, one may calculate the angles of illumination and detection in air necessary to achieve this condition. An example of this for a sapphire window is shown in FIG. 12. In this case, illumination fiber optic bundle 310 is inclined at a 60 degree angle with respect to the cylinder axis, while the detection fiber optic bundle 306 is inclined at 15.5 degrees to the cylinder axis on the opposite side of the axis from the illumination bundle, in order to achieve the 45 degree offset inside the sapphire window.

Figure 13:
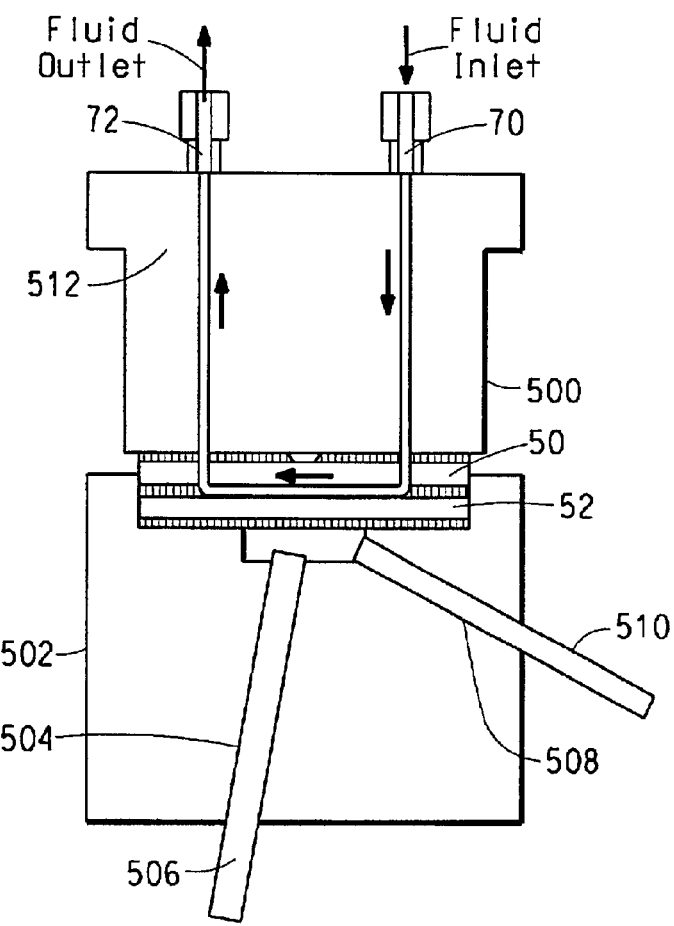
FIG. 13 is a front view of a further fluid analysis cell in accordance with this invention that takes into account the above correction factors of FIGS. 11 and 12.

So, using the concept shown in FIG.12 to achieve 45/0 illumimtric measurements in reflection mode, the wet cell design 500 for this embodiment is shown in FIG. 13, again utilizing fiber optic bundles as optical probes, with the probe angles as in FIG. 12. Embodiment 500, therefore, is the same as that of embodiment 300, except that the cell 500 has for its non-fluid-containing half 502, a probe channel 504 at an oblique angle to the cylinder axis for the detection fiber bundle 506, as well as one or more additional probe channels 508 with additional probe(s) 510 at an angle to the axis, on the opposite side of the axis to the detection probe, where the apex of the angle is on the axis of the cylinder and within the sample itself between the two windows in the cell. The angles of the probes will vary with the window material.

Figure 14:
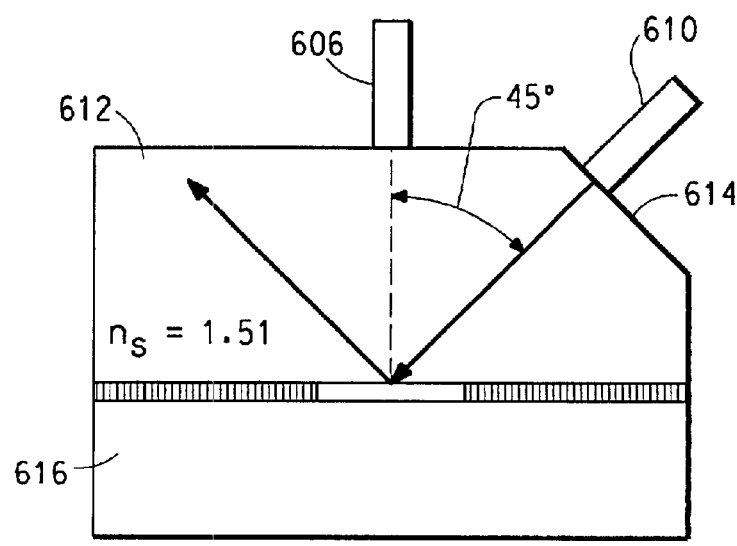
FIG. 14 is a schematic view of a fluid analysis cell window, which eliminates adjustments that may need to be made to the cell to correct for index of refraction mismatches.
Figure 15:
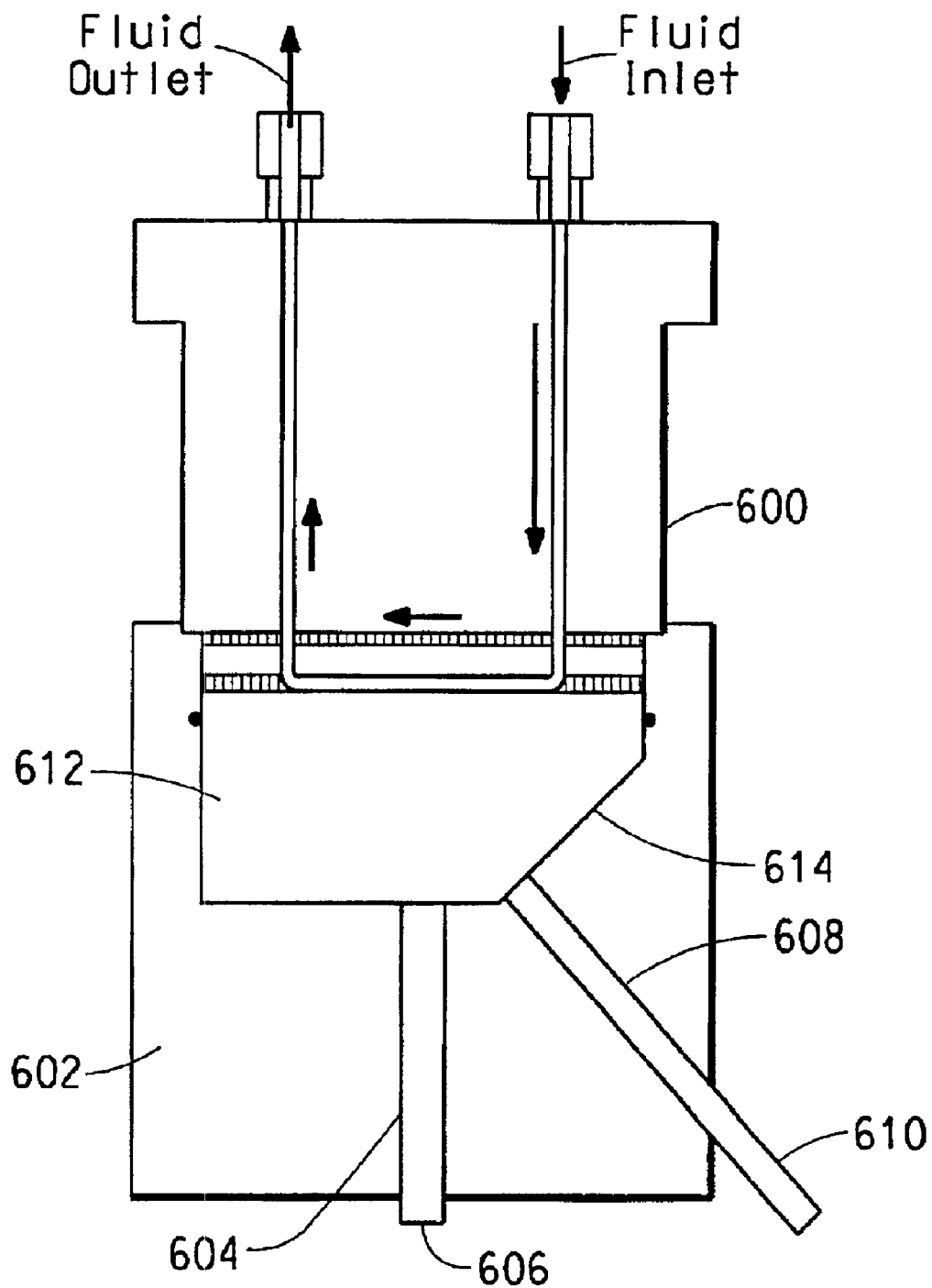
FIG. 15 is a front view of a further apparatus in accordance with this invention that takes into account the above correction factors of FIG. 14.

This is not, however, the only way to imbue a 45/0 geometry to the cell design. Indeed it is desirable to eliminate any air/window interface index of refraction effects. In order to do this, it is necessary that the fiber bundle probes couple to the window material normal to its surface. Thus to achieve any illumination or detection direction with respect to the sample surface that is anything other than normal, it is necessary that the window be at the appropriate angle with respect to the sample on the side of the window where the probe makes contact with it. In other words, the introduction to the window of one or more facets at the appropriate angles will allow both conditions to be met. In the case of 45/0 geometry, the window which makes contact with the optical fiber bundle probes would take on the design shown in FIG. 14. The wet cell design 600 for this embodiment is shown in FIG. 15 again utilizing fiber optic bundles as optical probes, with the probe/window placement as in FIG. 14. In this case, illumination fiber optic bundle 610 is inclined at a 45 degree angle with respect to the cylinder axis, but at 0 degrees with respect to the surface normal of the window 612, while the detection fiber optic bundle 606 is parallel to the cylinder axis and normal to the window, which thus achieves a true 45/0 geometry inside the window.

Also in this particular case, shown is a window material with index of refraction of 1.51, such as quartz, but it could be any material. It is, however, preferable to closely match the index of refraction of the window to that of the sample under study in order to reduce any index of refraction effects such as total internal reflection, as well as to reduce extraneous scattering effects. Embodiment 600, therefore, is the same as that of embodiment 300, with the cell 600 having for its non-fluid-containing half 602, a probe channel 604 down its axis for the detection fiber bundle 606, as well as one or more additional probe channels 608 with additional probe(s) 610 at an angle to the axis, where the apex of the angle is on the axis of the cylinder and within the sample itself between the two windows in the cell. The main difference between this and embodiment 300 is that the window 612 which provides the probe interface to the sample is cylindrical with one or more facets 614 cut into the end which interfaces with the optical fiber bundles or probes, such that the bundles or probes are always normal to the widow surface.

A further extension of the above design is to include multiple facets on the thicker window with such angles with respect to the sample surface so as to allow multiple detector probes to be placed at the flat, high and near-specular angles, as defined by the ASTM, for measurement of paints, tints, or dispersions containing interference materials such as metallic flake, pearl flakes or the like.

What is claimed is:

1. An apparatus for measuring the color properties of a fluid, comprising:

a fluid analysis cell having a cavity therein;

upper and lower light transmitting viewing windows which are transparent to visible light enclosing opposite ends of the cavity;

a spacer fixedly positioned in said cavity between said upper and lower viewing windows providing a fluid chamber where fluid flows between said windows;

a fluid inlet and outlet channel connected in fluid communication with said fluid chamber to enable fluid to flow into and out of said fluid chamber; and, a light transmitting and a light receiving probe positioned in any order above and below the upper and lower viewing windows, wherein the faces of each probe are in axial alignment with each other and are contiguous and flush with the viewing windows and orthogonal to the direction of flow but separated from the flow by the viewing windows, so that light transmittance measurements can be taken over the visible spectrum orthogonal to the direction of flow to determine the color properties of the fluid in the cell.

2. The apparatus of claim 1 in which a light source and a spectrophotometer are associated with and connected to the probes for directing light to the fluid analysis cell and detecting light therefrom respectively to measure color parameters of the fluid passing through the viewing windows by transmittance.

3. The apparatus of claim 2 in which the spectrophotometer is a dual beam spectrophotometer and the light source is a flash lamp.

4. The apparatus of claim 3 in which light is transmitted to the fluid analysis cell and received therefrom by means of single-fiber fiber optic cables. terminated in fiber optic probes which interface with the fluid analysis cell viewing windows.

5. The apparatus of claim 4 in which the viewing windows and probe faces are of sapphire glass and the spacer member is of brass.

6. The apparatus of claim 3 in which light is transmitted to the fluid analysis cell and received therefrom by means of fiber optic bundles which interface with the fluid analysis cell viewing windows.

7. The apparatus of claim 6 in which one of the transmission fiber optic bundles is interfaced to an integrating sphere having one of its portals contiguous with one of the analysis cell windows, so that diffuse as well as direct transmittance measurements over the visible spectrum can be made on the fluid sample being analyzed.

8. The apparatus of claim 6 in which an additional fiber optic bundle or probe is positioned at an angle other than normal to the fluid sample surface so that reflectance measurements over the visible spectrum can also be made on the fluid sample being analyzed.

9. The apparatus of claim 8 in which one of the analysis cell windows which interfaces with the fluid sample is replaced with a faceted cylinder of a material transparent to visible light.

10. The apparatus of claim 9 in which the surface of the cylinder distal from the fluid chamber and parallel thereto has one or more facets at an angle to the fluid sample surface, in order to interface with fiber optic bundles or probes, such that said bundles or probes are normal to each facet, for illumination of the sample and/or reception of the light therefrom at an angle other than normal to the surface of the sample, so that reflectance measurements over the visible spectrum can also be made on the fluid sample being analyzed.

11. The apparatus of claim 10 in which the spectrophotometer receives light from more than one of the fiber bundles or probes interfacing with the cylinder facets, and in which the angles of the facets conform with industrial standards such that measurements may be made on fluids containing interference materials.

12. The apparatus of claim 3 in which the flash lamp is covered by a shroud to provide connections for fiber optic cables or bundles which direct light to the spectrophotometer and fluid analysis cell.

13. The apparatus of claim 12 in which the shroud has a shutter assembly attached thereto for blocking light to the fluid analysis cell during photometric calibration of the dual-beam spectrophotometer in order to correct for stray light leakage from the reference side thereof to the sample side thereof during analysis of dark fluid samples.

14. The apparatus of claim 2 which further includes:
a pressure vessel, in which a fluid sample is placed, and which, by means of pressurization, delivers the sample to the fluid analysis cell:
a purged explosion-proof enclosure for containing all electrical/electronic components, as well as the light source for the instrument; and
an automatic pneumatically-controlled sample system for delivery of the sample to the fluid analysis chamber.

15. The apparatus of claim 2 in which the fluid analysis cell is cylindrical.

16. The apparatus or claim 2 in which the flow of fluid through the fluid analysis chamber is unidirectional and laminar at a uniform shear.

* * * * *